United States Patent
Tockman et al.

(10) Patent No.: US 7,477,946 B2
(45) Date of Patent: Jan. 13, 2009

(54) FIXATION DEVICE FOR CORONARY VENOUS LEAD

(75) Inventors: Bruce A. Tockman, Scandia, MN (US); Neil M. Becker, Fallbrook, CA (US); Cindy L. Sherman, Temecula, CA (US); Kevin M. Phillips, Murrieta, CA (US); Scott A. Stockmoe, Maple Grove, MN (US); Yongxing Zhang, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 486 days.

(21) Appl. No.: 11/114,730

(22) Filed: Apr. 26, 2005

(65) Prior Publication Data

US 2006/0241737 A1    Oct. 26, 2006

(51) Int. Cl.
    *A61N 1/05* (2006.01)
(52) U.S. Cl. .................. 607/126; 607/119; 607/122; 607/125
(58) Field of Classification Search .................. 607/119, 607/122, 125, 126, 130; 623/1.11
    See application file for complete search history.

(56) References Cited

U.S. PATENT DOCUMENTS

| | | |
|---|---|---|
| 4,819,661 A | 4/1989 | Heil, Jr. et al. |
| 4,827,940 A | 5/1989 | Mayer et al. |
| 5,221,261 A | 6/1993 | Termin et al. |
| 5,224,491 A | 7/1993 | Mehra |
| 5,449,372 A | 9/1995 | Schmaltz et al. |
| 5,514,174 A | 5/1996 | Heil, Jr. et al. |
| 5,531,779 A | 7/1996 | Dahl et al. |
| 5,649,906 A | 7/1997 | Gory et al. |
| 5,871,531 A | 2/1999 | Struble |
| 5,902,331 A | 5/1999 | Bonner et al. |
| 5,951,597 A | 9/1999 | Westlund et al. |
| 5,954,761 A | 9/1999 | Machek et al. |
| 6,129,750 A | 10/2000 | Tockman |
| 6,136,021 A | 10/2000 | Tockman et al. |
| 6,161,029 A | 12/2000 | Spreigl et al. |
| 6,178,356 B1 | 1/2001 | Chastain et al. |
| 6,397,109 B1 | 5/2002 | Cammilli et al. |
| 6,408,214 B1 | 6/2002 | Williams et al. |
| 6,510,347 B2 | 1/2003 | Borkan |
| 6,709,415 B2 | 3/2004 | Navia et al. |
| 6,711,443 B2 | 3/2004 | Osypka |
| 6,730,064 B2 | 5/2004 | Ragheb et al. |
| 6,774,278 B1 | 8/2004 | Ragheb et al. |
| 6,842,648 B2 | 1/2005 | Partridge et al. |

(Continued)

FOREIGN PATENT DOCUMENTS

EP        0795343 A2    9/1997

(Continued)

*Primary Examiner*—Carl H Layno
*Assistant Examiner*—Eugene T Wu
(74) *Attorney, Agent, or Firm*—Faegre & Benson LLP

(57) ABSTRACT

In one embodiment, the present invention provides a cardiac lead device including a fixation mechanism slidably attached to the lead such that when the fixation mechanism is expanded into contact with a body lumen, the lead may be moved relative to the fixation mechanism if desired. Such lead movement may be limited by complimentary structure on the lead body and the fixation mechanism that prevents the lead from moving unless sufficient force is applied to the lead.

17 Claims, 7 Drawing Sheets

U.S. PATENT DOCUMENTS

| | | |
|---|---|---|
| 2002/0026228 A1 | 2/2002 | Schauerte |
| 2002/0045926 A1 | 4/2002 | Heil, Jr. et al. |
| 2002/0082679 A1 | 6/2002 | Sirhan et al. |
| 2002/0103522 A1 | 8/2002 | Swoyer et al. |
| 2003/0065374 A1 | 4/2003 | Honeck |
| 2003/0083646 A1 | 5/2003 | Sirhan et al. |
| 2003/0139801 A1 | 7/2003 | Sirhan et al. |
| 2003/0144727 A1 | 7/2003 | Rosenthal et al. |
| 2003/0163184 A1 | 8/2003 | Scheiner et al. |
| 2003/0199961 A1 | 10/2003 | Bjorklund |
| 2003/0204231 A1 | 10/2003 | Hine et al. |
| 2003/0220677 A1 | 11/2003 | Doan et al. |
| 2004/0059404 A1 | 3/2004 | Bjorklund et al. |
| 2004/0062852 A1 | 4/2004 | Schroeder et al. |
| 2005/0070985 A1 | 3/2005 | Knapp et al. |
| 2005/0080472 A1 | 4/2005 | Atkinson |
| 2005/0131511 A1 | 6/2005 | Westlund |

FOREIGN PATENT DOCUMENTS

| | | |
|---|---|---|
| WO | 03092799 A1 | 11/2003 |
| WO | 2004060478 A1 | 7/2004 |

FIXATION DEVICE FOR CORONARY VENOUS LEAD

TECHNICAL FIELD

The present invention relates to implantable medical devices and, in particular, to fixation of cardiac leads in a patient's vascular system.

BACKGROUND

Cardiac function management systems are used to treat arrhythmias and other abnormal heart conditions. Such systems generally include cardiac leads, which are implanted in or about the heart, for delivering an electrical pulse to the cardiac muscle, for sensing electrical signals produced in the cardiac muscle, or for both delivering and sensing. The lead typically consists of a flexible conductor, defining a central channel or lumen, surrounded by an insulating tube or sheath extending from an electrode at the distal end to a connector pin at the proximal end.

Cardiac lead placement may be accomplished by introducing the lead through a major blood vessel and advancing a distal end of the lead to a final destination in or near the heart. To facilitate cannulation of the vasculature, it is often helpful to first advance a guiding catheter through the desired vascular path. One difficulty with implanting leads in this fashion is that the cardiac lead has a tendency to become dislodged from its desired location during or after lead implantation. For example, when a clinician withdraws the guiding catheter, the lead may dislodge or otherwise reposition. Until tissue ingrowth ultimately fixes the lead at the desired site, cardiac leads may also become dislodged by subsequent physiological activity.

A variety of screws, anchors, and other devices have been secured to cardiac leads to affix the leads at a desired location in a patient's vasculature. Nonetheless, there is a need in the art for a cardiac lead having a fixation mechanism which effectively affixes the cardiac lead at a desired position, but which also allows the lead to be repositioned within or removed from the patient's vasculature, even after an extended implantation period.

SUMMARY

In one embodiment, the present invention provides a cardiac lead system adapted for anchoring in a vessel. The system includes a conductive lead body and an expandable fixation mechanism. The lead body has a proximal end and a distal end and defines a lead lumen extending between the proximal and distal ends. The expandable fixation mechanism has an expanded position adapted to engage an inner surface of the vessel, and is slidably secured to an outer surface of the lead body. The lead body and the fixation mechanism include respective first and second structures that are adapted to contact each other to resist relative longitudinal movement.

The first structure on the lead body may include one or more stops, curves, bends, coils, ridges or other protrusions on the lead body the second structure may include one or more rings connected to the fixation mechanism and encircling the lead body. In one embodiment, the system further includes a stylet, which may be inserted into the lead body to straighten any curves, bends, or ridges in the lead body, thus reducing the overall diameter of portions of the lead body.

The fixation mechanism may be self-expanding or balloon-expanding. For self-expanding embodiments, the fixation mechanism may be compressed by an outer guide or by a dissolvable material which dissolves upon contacting bodily fluid. In one embodiment, the fixation mechanism is formed similarly to a conventional stent.

In another embodiment, the present invention provides a cardiac lead device including a conductive lead body and an expandable fixation mechanism as reported above, means for compressing the fixation mechanism, and means for resisting the relative movement when the fixation mechanism is secured to the outer surface of the tubular wall of the lead body. The means for compressing the fixation mechanism may include one or more guides through which the lead body and/or fixation mechanism are slidably movable. The means for compressing may also include a dissolvable material as reported above. The means for resisting relative movement may include the first and/or second structure reported above.

The present invention also provides a method for implanting a cardiac lead device in a body lumen. A cardiac lead device as reported herein is guided into the body lumen. A fixation mechanism, which is slidably securable to the lead body, is then deployed from a compressed position to an expanded position to engage the internal wall of the body lumen. The lead can be moved relative to the expanded fixation mechanism in order to reposition the lead. Prior to guiding the lead device, one or more guides may be inserted into the body lumen to facilitate the lead implantation process.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Figure 1:
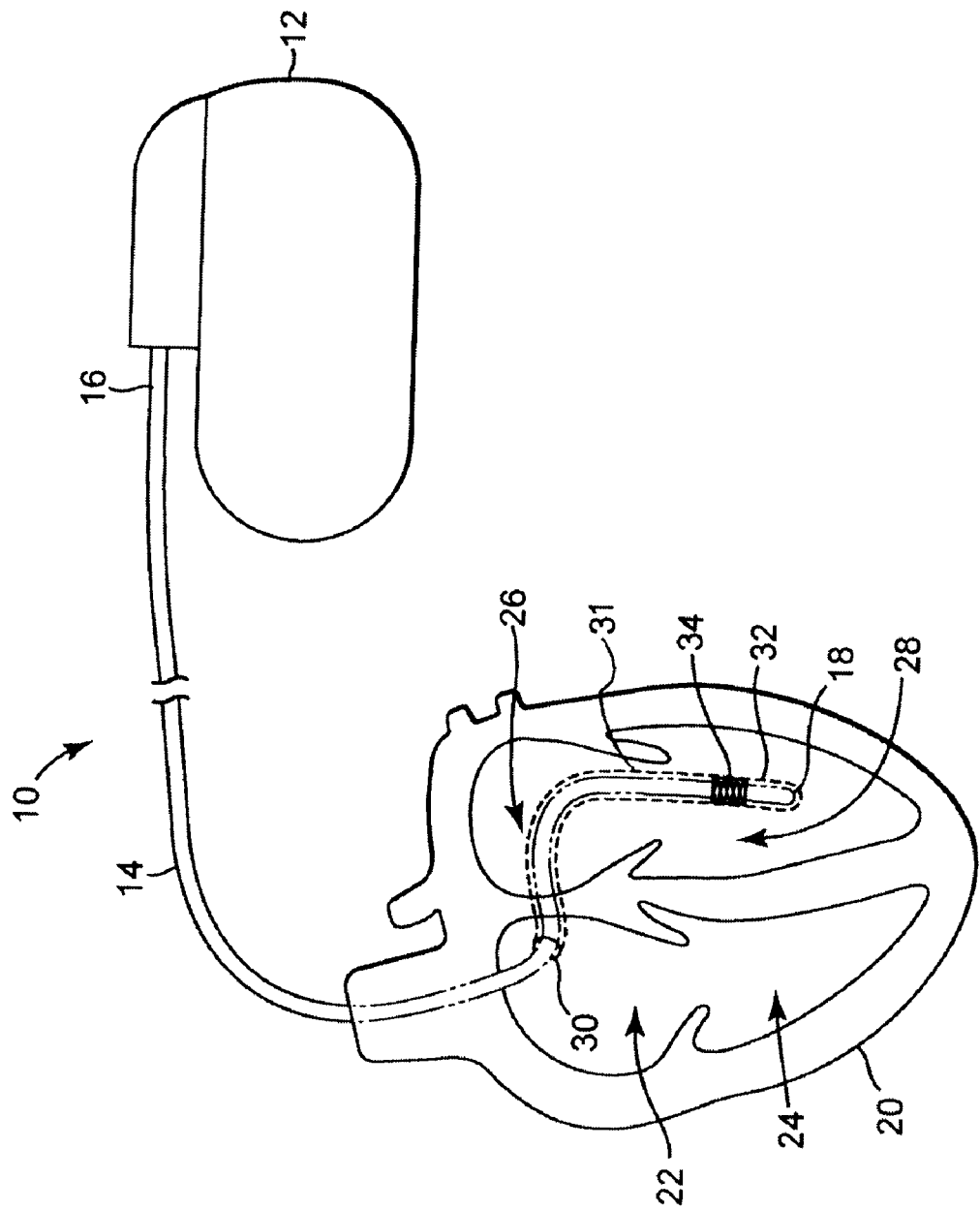
FIG. 1 shows a schematic view of a cardiac lead implanted in a patient's vasculature according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic drawing of a cardiac rhythm management device 12 coupled to an intravascular endocardial lead 14 having a proximal end 16 and a distal end 18. Distal portions of the lead 14 are disposed in the patient's heart 20, which includes a right atrium 22, a right ventricle 24, a left atrium 26, and a left ventricle 28. In the embodiment illustrated in FIG. 1, the distal end 18 of lead 14 is transvenously guided into the right atrium 22, through a coronary sinus 30, and into a cardiac vein 31. The illustrated disposition of the lead 14 may be used for delivering pacing and/or defibrillation energy through any cardiac vessel, including the cardiac sinus 30, coronary veins or pulmonary artery, to the left ventricle 28 for the treatment of cardiac arrhythmias.

FIGS. 2-5 show cross-sectional views of a vessel 31 into which the cardiac lead 14 has been implanted. The cardiac lead 14 generally includes a lead body 33 and an expandable fixation mechanism 34, which is secured to the lead body 33. The lead body 33 has a proximal end 16 (see FIG. 1) and a distal end 18 and at least one lead lumen 38 extending between the proximal and distal ends 16, 18. The lead body 33 further includes at least one electrode 37 at distal end 18 for delivering electrical pulses to a patient's heart. Although not illustrated, the electrode 37 may be affixed to the wall of vessel 31.

The fixation mechanism 34 is configured to contact the vessel 31 when in an expanded position as shown in FIGS. 2-5. The fixation mechanism 34 shown in FIGS. 2-5 is configured in a stent-like form. Other shapes and configurations may also be suitable for embodiments of the present invention. The fixation mechanism 34 may be formed from conventional stent materials, for example, stainless steel, nitinol, or shape memory alloys or polymers. In a particular embodiment, the fixation mechanism 34 is (or is a modified version of) a Palmaz-Shatz type stent commonly used in vascular intervention procedures. In another embodiment, the fixation mechanism 34 is partially or completely formed from a biodegradable and or dissolvable material that degrades when contacted with body fluid.

The fixation mechanism 34, is slidably secured to the lead body 33 such that the lead body 33 is selectively moveable relative to the fixation mechanism 34 along the longitudinal path of the vessel 31 when the fixation mechanism 34 is in the expanded position shown. Such selective relative movement is accomplished by providing both the lead body 33 and the fixation mechanism 34 with cooperating or corresponding structures as described in detail below.

The structure on the lead body 33 may be configured to increase a major dimension (e.g. diameter) of the lead body 33 at select locations. Numerous configurations may be employed for the structure on the lead body 33. In the embodiment illustrated in FIG. 2, for example, the lead body 33 includes one or more coiled or looped portions 44, which cooperate with structure on the fixation mechanism 34 to limit undesired or unintentional longitudinal movement of the lead body 33. In an alternate embodiment, the structure includes a two-dimensional shape such as a sinusoidal shape or a J-bend.

Figure 4:
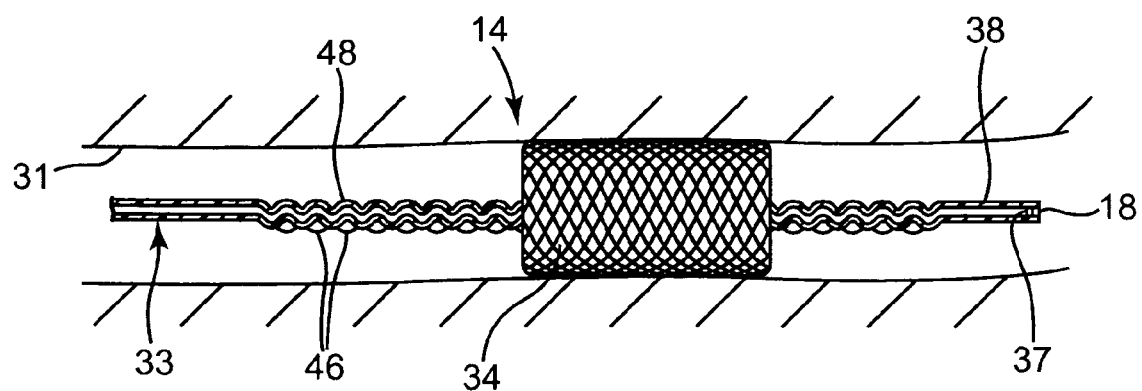
FIG. 4 shows a distal portion of a cardiac lead implanted in a patient's vasculature according to another embodiment of the present invention.

The embodiment illustrated in FIG. 4 includes protrusions 46 secured along a plurality of ridges 48 formed in the lead body 33. The protrusions 46 may be formed as bumps, spheres, ears, rings, or other shapes formed on and extending from the surface of the lead body 33. The protrusions 46 may be formed from silicone or other biocompatible materials and may remain substantially permanently secured to the lead body 33 or may be biodegradable.

Figure 3:
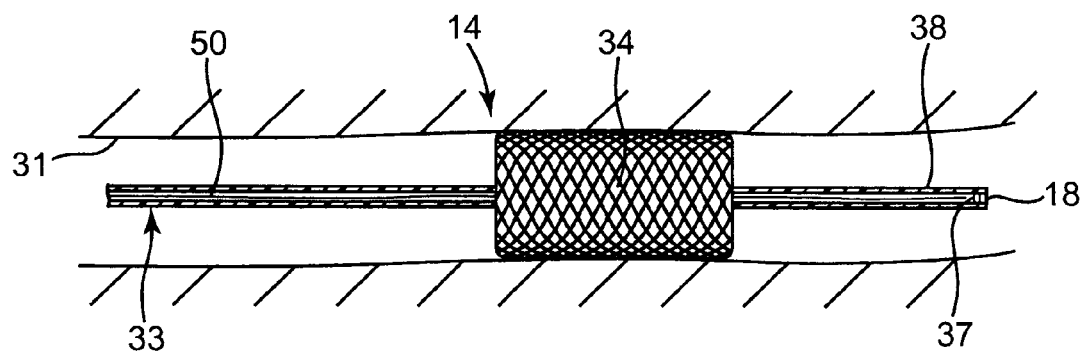
FIG. 3 illustrates the embodiment of FIG. 2 after insertion of a stylet into a lumen of the cardiac lead.

The looped portions 44, protrusions 46, or ridges 48 may be positioned anywhere along the length of the lead body 33. In the illustrated embodiments, structure is located both proximal and distal to the fixation mechanism 34 to allow for a range of proximal and distal movement of lead body 33. Other configurations may also be appropriate depending on the specific application of the cardiac lead 14. Furthermore, although FIGS. 3-4 show specific structures for limiting movement of the lead body 33, it should be appreciated that a wide range of structures, either individually or in combination, may be used in embodiments of the present invention. The loops 44, protrusions 46, or ridges 48 may be spaced at various adjustment intervals depending on the magnitude of adjustments desired. In one embodiment, for example, these structures are located between about 1 and about 10 millimeters apart, or more preferably between about 2 and about 5 millimeters apart, along the lead body 33.

Figure 2:
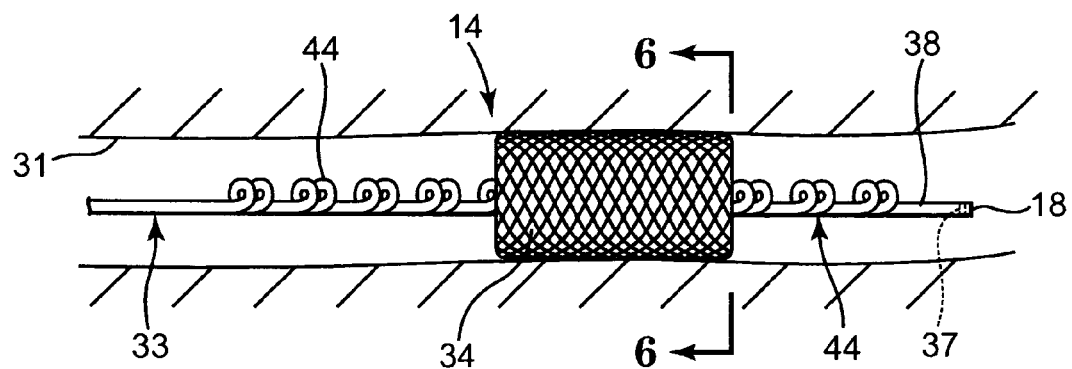
FIG. 2 shows a schematic view of a distal portion of a cardiac lead according to an embodiment of the present invention implanted in a patient's vasculature.
Figure 6A:
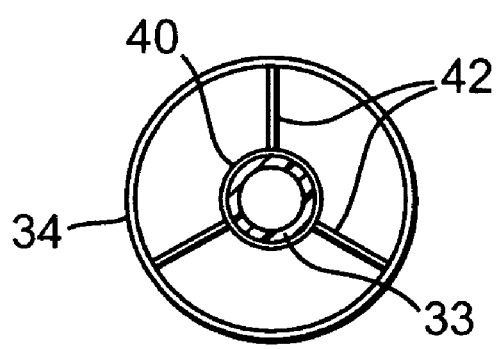
FIGS. 6A-6D show end plan views of multiple embodiments of the present invention.
Figure 6B:
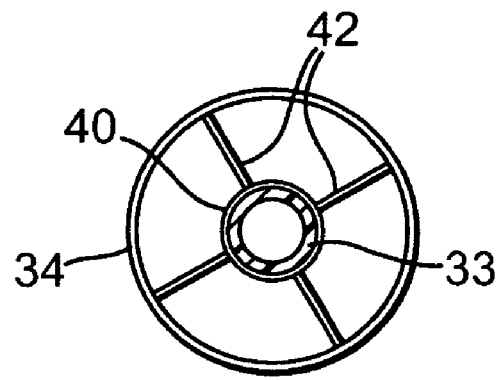
Figure 6C:
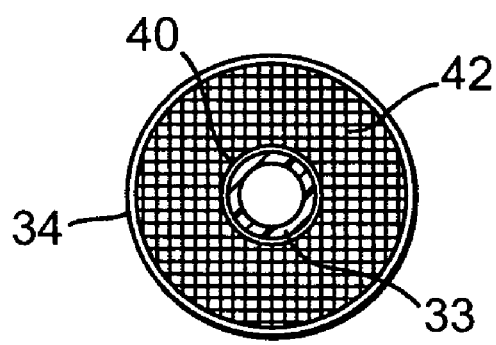
Figure 6D:
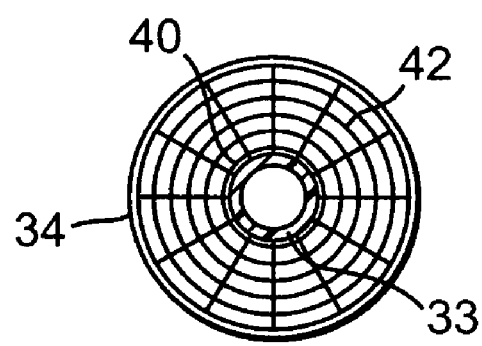

FIGS. 6A-6C show plan views of the cardiac lead 14 from the perspective of the line 6-6 shown in FIG. 2. As shown in FIGS. 6A-6D, the fixation mechanism 34 includes one or more fixation rings 40 which contact or otherwise interact with structure on the lead body 33 to provide selective movement of the lead body 33. The fixation rings 40 generally encircle the lead body 33, and are generally connected to the outside (i.e. vessel engaging) surface of the fixation mechanism 34 via struts 42. As further shown in FIGS. 6A-6D, the struts 42 may be have a variety of configurations. The fixation rings 40 may be formed anywhere along the length of the fixation mechanism 34, but in one embodiment, the fixation rings 40 are disposed on opposing ends of the fixation mechanism 34.

The fixation rings 40 and struts 42 may be formed from a variety of materials, including materials commonly used to form stents. In certain embodiments either or both of the rings 40 and the struts 42 may be formed from an elastic, string, fibrous, or thread-like material. Additionally the fixation rings 40 and the struts 42 may be formed to be biodegradable and/or dissolvable upon contact with bodily fluid, or to remain substantially permanently in the vessel 31. In one embodiment, the fixation rings 40 and the struts 42 may be formed to biodegrade after a period of time sufficient to allow the lead body to become secured within the vessel 31 by tissue in-growth. For example, the fixation mechanism 34 could be temporarily fixed to the lead body with a resorbable material that would dissolve over a period of weeks or months to allow extraction of the lead at a later date.

As shown in FIGS. 2 and 4, the structures disposed on both the lead body 33 and the fixation mechanism 34 resist longitudinal movement of the lead body 33 relative to the fixation mechanism 34 because the structure on the lead body 33 (i.e. coiled portions 44, protrusions 46 and/or ridges 48) has a major dimension that is greater than the diameter of the fixation rings 40 such that longitudinal movement of the lead body 33 is limited or selectively prevented.

Figure 5:
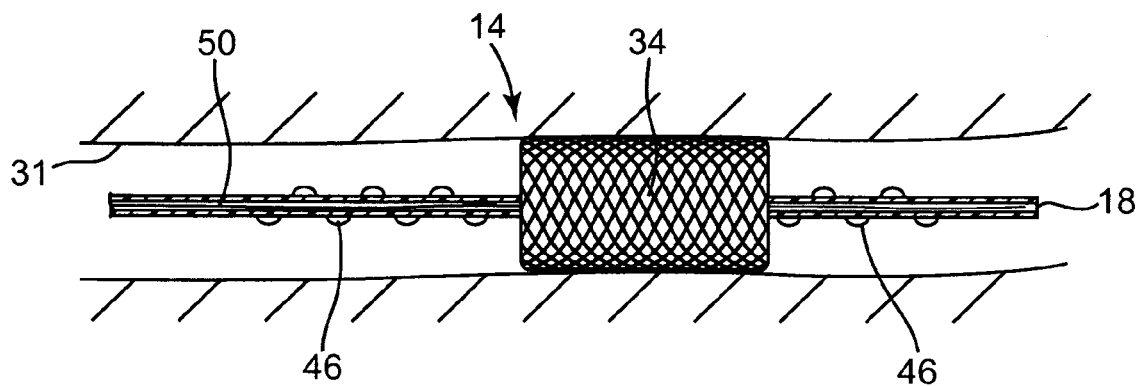
FIG. 5 illustrates the embodiment of FIG. 4 after insertion of a stylet into a lumen of the cardiac lead.

To reposition the lead body 33 according to one embodiment, the major dimension of the lead body 33 in the vicinity of the fixation mechanism 34 may be reduced to a size that is smaller than the diameter of the fixation rings 40, by inserting a stylet or guidewire into the lead lumen 38. For example, FIG. 3 shows the embodiment of FIG. 2 after inserting a stylet or guidewire 50 such that the coiled portions 44 are straightened. FIG. 5 shows the embodiment of FIG. 4 after inserting a stylet or guidewire 50 such that the ridges 48 are straightened. In both cases, the lead body 33 becomes movable relative to the fixation mechanism 34 along the longitudinal path of the vessel 31. After repositioning the lead body 33, the stylet or guidewire 50 may be removed such that the structure returns to the shape shown in FIGS. 2 and 4, which again limits longitudinal movement of the lead 33 with respect to the fixation mechanism 34. According to another embodiment, instead of changing the major diameter of the lead, the interacting structures on the lead body 33 and the fixation rings 40 have sufficient flexibility to allow the structures to pass through the rings upon application of a sufficient force at the proximal end 16 of the lead body 33.

Figure 7:
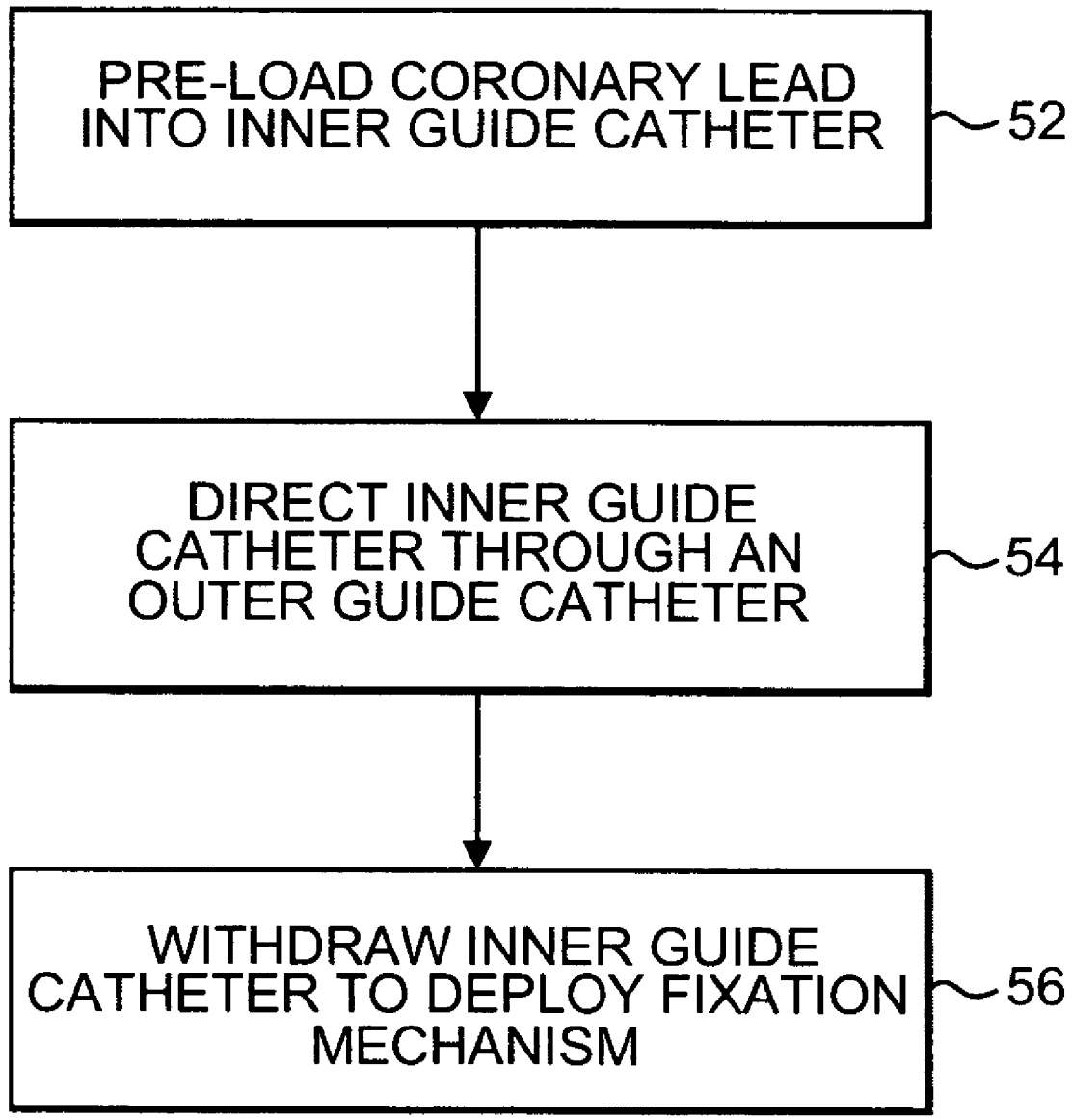
FIG. 7 is a flowchart illustrating a method for implanting a cardiac lead according to one embodiment of the present invention.
Figure 8:
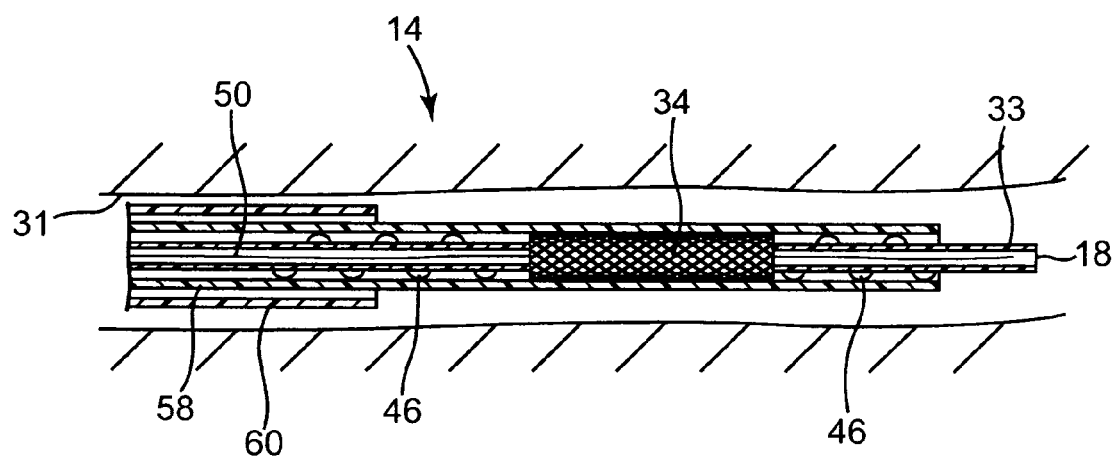
FIG. 8 shows a cardiac lead being implanted according to the method described in FIG. 7.

FIGS. 7-8 depict a method of implanting the cardiac lead 14 according to an embodiment of the present invention. FIG. 7 is a flow-chart showing a method of implanting the cardiac lead 14 according to one embodiment of the present invention. The cardiac lead 14 is pre-loaded into an inner guide catheter 58 such that the fixation mechanism 34 is in a compressed position (block 52). The inner guide catheter 58 is then directed through the patient's vasculature, optionally through an outside guide catheter or sheath 60, to a desired location in the patient's vasculature (block 54) as shown in FIG. 8. The inner guide catheter 58 is then withdrawn such that the fixation mechanism 34 deploys to an expanded position (block 56) shown in FIGS. 2-5. The fixation mechanism 34, in this embodiment, may expand by, for example, self-expansion or balloon expansion. After the fixation mechanism 34 is expanded and secured to the wall of the vessel 31, the longitudinal position of the lead 33 may be adjusted. The stylet or guidewire 50 is then removed, which allows the lead 33 to resume its default shape (see, for example, FIGS. 2 and 4) having an increased major diameter, which, in turn, limits or resists further longitudinal movement of the lead 33.

In a variation of the method described in FIGS. 7-8, the fixation mechanism 34 may be fixed to the lead body in a compressed state with a dissolvable material such as manitol. The lead 14 is inserted through inner guide catheter 58 until positioned as desired. The lead 14 could then be advanced out of the inner guide catheter 58 to the desired position, which would also expose the dissolvable material to blood. After a short period of time the dissolvable material would dissolve, allowing the fixation mechanism 34 to expand and contact the vessel wall.

Figure 10:
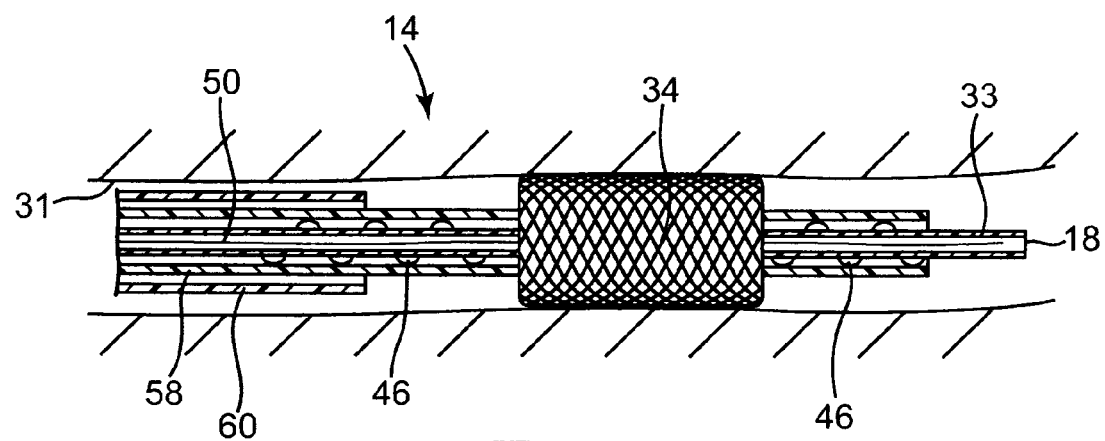
FIG. 10 illustrates a cardiac lead implanted according to the method illustrated in FIG. 9.
Figure 9:
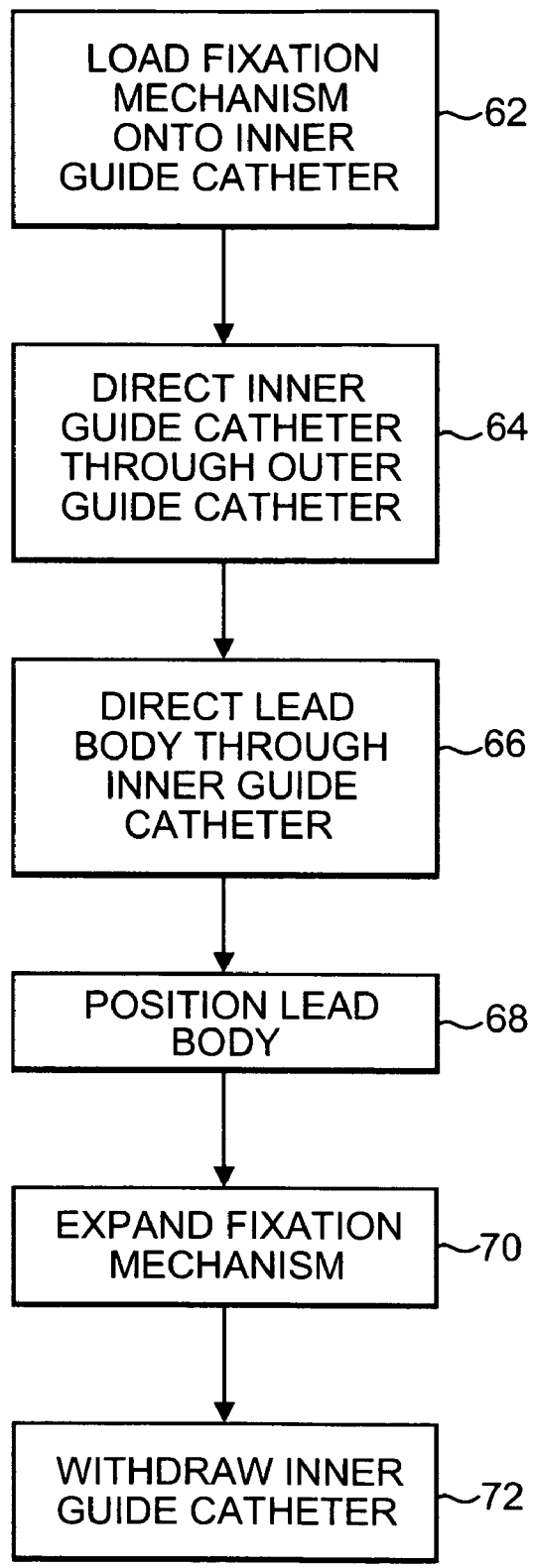
FIG. 9 is a flowchart describing an alternate method for implanting a cardiac lead according to one embodiment of the present invention.

FIGS. 9-10 depict a method of implanting the cardiac lead 14 according to another embodiment of the present invention. FIG. 9 is a flow-chart summarizing a method of implanting the cardiac lead 14 according to an embodiment of the present invention, in which the fixation mechanism 34 is initially positioned on an outer surface of the inner guide catheter 58 (block 62) with an optional inflation balloon 59 disposed between the fixation mechanism 34 and the inner guide catheter 58. The inner guide catheter 58 is then directed through an outside guide catheter 60 and into a desired location in a patient's vasculature (block 64). The lead body 33 is then directed through the inner guide catheter 58 (block 66) until the distal end 18 of the lead body 33 extends past the distal end of the inner guide catheter 58 and into a desired location (block 66) as shown in FIG. 10. The fixation mechanism 34 is then expanded via self-expansion or by inflating the optional balloon 59 in a conventional manner (block 70). The inner guide catheter 58 is then withdrawn such that the fixation rings 40 encircle the lead body 33 as shown in FIGS. 2-5 (block 72). After the fixation mechanism 34 is expanded and secured to the wall of the vessel 31, the longitudinal position of the lead 33 may be adjusted. The stylet or guidewire 50 is then removed, which allows the lead 33 to resume its default shape (see, for example, FIGS. 2 and 4) having an increased major diameter, which, in turn, limits or resists further longitudinal movement of the lead 33.

In a variation to the method shown in FIGS. 9-10 and described above, the fixation mechanism 34 is disposed on the inner guide catheter 58 and is pre-loaded into the outside guide catheter 60. After positioning the inner and outer guide catheters 58, 60 and the lead body 33 as described above, a tube or other structure (not shown) may be directed between the inner and outer guide catheters 58, 60 to deploy the fixation mechanism 34 into an expanded position shown in FIGS. 2-5.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. A cardiac lead system adapted for anchoring in a vessel, the system comprising:
    a lead body including at least one electrode and having a proximal end and a distal end, the lead body defining at least one lead lumen extending between the proximal and distal ends and a plurality of stops located on an outer surface of the lead body; and
    an expandable fixation mechanism having an expanded position adapted to engage an inner surface of the vessel and including a structure slidable over an outer surface of the lead body between the plurality of stops, such that the lead body is adapted to move longitudinally relative to the fixation mechanism when the fixation mechanism is in the expanded position; and
    wherein the plurality of stops are adapted to contact the structure to resist the longitudinal movement of the lead body relative to the fixation mechanism when the fixation mechanism is in the expanded position.

2. The system of claim 1 where the plurality of stops include curves, bends, coils, or ridges on the lead body.

3. The system of claim 2 further comprising a stylet and wherein a diameter of the plurality of stops is adapted to be substantially reduced upon inserting the stylet through the lead lumen.

4. The system of claim 1 further comprising a guide having a proximal end and a distal end and including a tubular wall defining a lumen extending between the proximal and distal ends, wherein the lead body and fixation mechanism are slidable within the guide lumen.

5. The system of claim 4 wherein the fixation mechanism remains compressed when disposed within the lumen of the guide, and expands upon deployment from the lumen of the guide.

6. The system of claim 1 wherein the plurality of stops includes at least one protrusion extending radially from the lead body.

7. The system of claim 1 wherein the structure includes at least one ring which encircles and slides relative to the outer surface of the lead body.

8. The system of claim 1 wherein the fixation mechanism comprises a stent-like configuration.

9. The system of claim 1 wherein at least a portion of the plurality of stops or the structure dissolves over a period of time after being contacted with body fluid.

10. The cardiac lead system according to claim 1, wherein a first stop is located proximal to the structure of the fixation mechanism and a second stop is located distal to the structure of the fixation mechanism such that the lead body is selectively moveable relative to the fixation mechanism in either a proximal or a distal direction between the first and second stops.

11. A cardiac lead device comprising:
   a lead body having a proximal end and a distal end, the lead body defining at least one lead lumen extending between the proximal and distal ends; and
   an expandable fixation mechanism slidable on an outer surface of the lead body when the fixation member is in an expanded position such that the lead body can move relative to the fixation member when the fixation member engages an inner surface of a vessed;
   means for compressing the fixation mechanism from the expanded position such that the fixation mechanism is selectively deployable within a body lumen; and
   means for resisting the movement of the lead body relative to the fixation mechanism at a plurality of predetermined positions when the fixation mechanism is in the expanded position.

12. The device of claim 11 wherein the means for compressing the fixation mechanism includes a guide having a lumen configured to slidably receive the lead body.

13. The device of claim 11 wherein the means for compressing the fixation mechanism includes a dissolvable material which is adapted to dissolve upon contacting a bodily fluid.

14. The device of claim 11 wherein the means for resisting movement includes at least one curve, bend, coil, ridge or protrusion on the lead body.

15. The device of claim 11 wherein the means for resisting movement includes at least one ring which is secured to the fixation mechanism and encircles the outer surface of the lead body.

16. A cardiac lead system adapted for anchoring in a vessel, the system comprising:
   a lead body including at least one electrode and having a proximal end and a distal end, the lead body defining at least one lead lumen extending between the proximal and distal ends;
   an expandable fixation mechanism having an expanded position adapted to engage an inner surface of the vessel, the expandable fixation mechanism being slideable on an outer surface of the lead body;
   a first structure located on the lead body, wherein the first structure includes at least one curve, bend, coil, or ridge on the lead body;
   a second structure located on the fixation mechanism, wherein the first structure and the second structure are adapted to contact each other to resist longitudinal movement of the lead body relative to the fixation mechanism; and
   a stylet, wherein a diameter of the first structure is adapted to be substantially reduced upon inserting the stylet through the lead lumen.

17. The cardiac lead system according to claim 16, wherein the first structure includes a plurality of first structures located on the lead body adapted to contact and cooperate with the second structure on the fixation mechanism such that the lead body is selectively moveable relative to the fixation mechanism in a longitudinal direction.

* * * * *